(12) United States Patent
Holzki et al.

(10) Patent No.: US 9,389,177 B2
(45) Date of Patent: Jul. 12, 2016

(54) METHOD AND DEVICE FOR ANALYSIS OF A FLUID BY MEANS OF EVANESCENCE FIELD SPECTROSCOPY AND DIELECTROPHORESIS

(71) Applicant: FRAUNHOFER-GESELLSCHAFT ZUR FORDERUNG DER ANGEWANDTEN FORSCHUNG E.V., Munich (DE)

(72) Inventors: Markus Holzki, Wörrstadt (DE); Thomas Klotzbücher, Mommenheim (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 113 days.

(21) Appl. No.: 14/353,527
(22) PCT Filed: Oct. 26, 2012
(86) PCT No.: PCT/EP2012/071263
§ 371 (c)(1),
(2) Date: Apr. 23, 2014
(87) PCT Pub. No.: WO2013/060846
PCT Pub. Date: May 2, 2013

(65) Prior Publication Data
US 2014/0252214 A1 Sep. 11, 2014

(30) Foreign Application Priority Data
Oct. 28, 2011 (DE) .......................... 10 2011 085 394

(51) Int. Cl.
*G01N 21/552* (2014.01)
*G01N 21/55* (2014.01)
*G01D 5/26* (2006.01)
*G01N 21/17* (2006.01)

(52) U.S. Cl.
CPC ................ *G01N 21/55* (2013.01); *G01D 5/268* (2013.01); *G01N 21/552* (2013.01); *G01N 2021/1721* (2013.01)

(58) Field of Classification Search
CPC ...................................................... G01N 27/26
USPC .................................. 250/458.1, 461.1, 461.2
See application file for complete search history.

(56) References Cited

U.S. PATENT DOCUMENTS

| 6,790,671 B1 * | 9/2004 | Austin .................. B82Y 20/00 204/155 |
| 6,899,849 B2 | 5/2005 | Meinhart et al. |
| 2006/0228257 A1 | 10/2006 | Hughes et al. |

FOREIGN PATENT DOCUMENTS

| DE | 102 51 893 A1 | 5/2004 |
| EP | 0 594 838 B1 | 2/1996 |

(Continued)

OTHER PUBLICATIONS

Kayani, et al., Interaction of Guided Light in Rib Polymer Waveguides with Dielectrophoretically Controlled Nanoparticles, Microfluid Nanofluid, 2011, vol. 11, pp. 93-104.

(Continued)

*Primary Examiner* — Renee D Chavez
(74) *Attorney, Agent, or Firm* — Hudak, Shunk & Farine Co. LPA

(57) ABSTRACT

A device for analyzing a fluid by evanescence field spectroscopy. The device includes a waveguide, a source of electromagnetic radiation coupled to the waveguide on the entry side, and a detector coupled to the waveguide on the exit side for detecting electromagnetic radiation, wherein the waveguide is arranged in contact with the fluid in at least certain sections between its entry side and its exit side. An electrode arrangement is also provided, which is designed to generate an inhomogeneous electric field in the direct environment of the waveguide, said field exerting a dielectrophoretic force on polarisable particles in the fluid, which moves these particles towards or away from the waveguide. A corresponding method is presented.

19 Claims, 5 Drawing Sheets

(56) References Cited

FOREIGN PATENT DOCUMENTS

| | | |
|---|---|---|
| JP | 09 257702 A | 10/1997 |
| WO | 2004 074819 A1 | 9/2004 |
| WO | 2004 113886 A1 | 12/2004 |
| WO | 200720443 A1 | 2/2007 |

OTHER PUBLICATIONS

Hoettges, et al., Optimizing Particle Collection for Enhanced Surface-Based Biosensors, IEEE Engineering in Medicine and Biology Magazine, Nov. 12, 2003, pp. 68-74.

Katarzyna, et al., Development of an Infrared Sensor for On-line Analysis of Lubricant Deterioration, IEEE, 2003, pp. 903-908.

Mizaikoff, Meas. Sci. Technol., vol. 10, 1999, pp. 1185-1194.

Villatoro, et al., In-Line Optical Fiber Sensors based on Cladded Multimode Tapered Fibers, Applied Optics, vol. 43, No. 32, Nov. 2004, pp. 5933-5938.

Sheeba, et al., Fibre Optic Sensor for the Detection of Adulterant Traces in Coconut Oil, Meas. Sci. Technol., vol. 16, 2005, pp. 2247-2250.

* cited by examiner

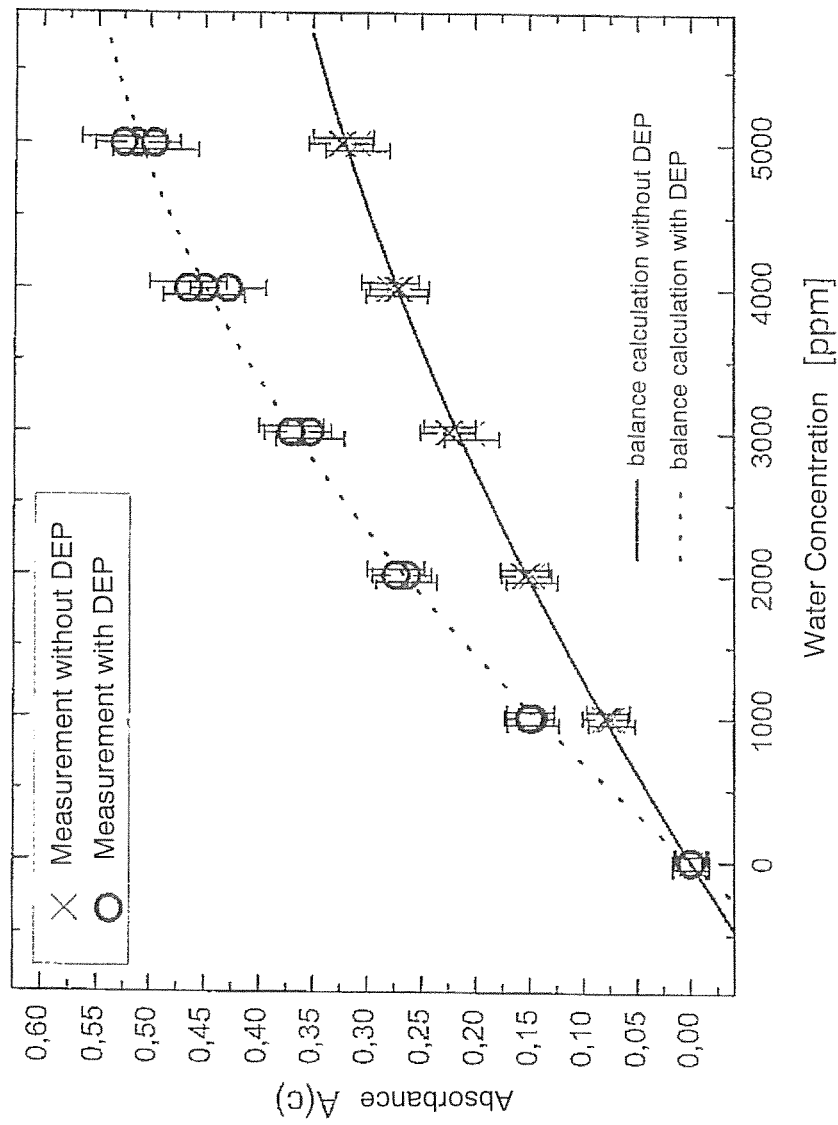

METHOD AND DEVICE FOR ANALYSIS OF A FLUID BY MEANS OF EVANESCENCE FIELD SPECTROSCOPY AND DIELECTROPHORESIS

FIELD OF THE INVENTION

The invention relates to a method for analyzing a fluid wherein electromagnetic radiation is coupled to a waveguide on the entry side, arranged in contact with the fluid in at least certain sections, moves through it undergoing total internal reflection, and is coupled out and detected at the exit side, it being possible to detect an attenuation of the electromagnetic radiation. The invention moreover relates to a device for carrying out this method, with a waveguide, a source of electromagnetic radiation coupled to the waveguide at the entry side, and a detector coupled to the waveguide on the exit side for detecting electromagnetic radiation, wherein the waveguide is arranged in contact with the fluid in at least certain sections between its entry side and its exit side.

BACKGROUND OF THE INVENTION

The above described method makes use of the effect that an evanescence field is formed on the surface of a waveguide when electromagnetic radiation is moved through a waveguide (by total reflection), which gives off no energy to the surroundings when no perturbations are present. But if a perturbation in the form of an absorbing medium is present in this zone, which has a thickness of not more than approximately one wavelength of the electromagnetic radiation coupled in, it can be coupled to the evanescent field and extract energy from it. By waveguide is meant here the part carrying the electromagnetic radiation. For example, if an optical core/cladding fiber is used, the core of the fiber is to be understood as the waveguide in the above sense.

The physical phenomenon is used in evanescence field spectroscopy, also known as ATR ("attenuated total reflection") technology, for the detection of specific radiation-absorbing substances in fluids. This technology can also be used, for example, in the spectroscopy of strongly absorbing media, such as lubricants containing soot particles, especially oils, which are not suitable for the classical absorption spectroscopy on account of too intense and broad-band attenuation of the radiation and therefore less useful signal dynamics, or at least cannot produce any reliable findings. Sample applications for evanescence field spectroscopy are given in the publications DE 102 51 893 A1, WO 2004/113886 A1 or EP 0594838 B1.

Starting from this known method, measures have been discussed in many scientific publications for boosting the sensitivity of evanescence field spectroscopy. Merely as examples, reference is made to the works of Kudlaty, et al., Development of an infrared sensor for on-line analysis of lubricant deterioration, Sensors, Proceedings of IEEE (2003), 2, 903; Mizaikoff, Mid-infrared evanescent wave sensor—a novel approach for subsea monitoring, Meas. Sci. Technol. 10 (1999), 1185; Villatoro et al., In-line optical fiber sensors based on cladded multimode optical fibers, Appl. Opt. 43 (2004), 5933 or Sheeba, Fibre optic sensors for the detection of adulterant traces in coconut oil, Mess. Sci. Technol. 16 (2005), 2247.

In the publications US 2006/0228257 A1 and U.S. Pat. No. 6,899,849 B2, methods of evanescent field measurement on biological specimens are discussed, which are supported by means of electric fields that cause an electroosmotic or dielectrophoretic flux in the medium being studied.

All of the known proposal are addressed to specific applications and therefore have the same specific drawbacks in other application instances. For example, one can mention a lack of suitability for analysis of dispersions or emulsions, expensive techniques for functionalizing the waveguide, lack of long-term stability of the corresponding coatings, slow response times and poor irreversibility of diffusion-controlled processes and quite generally expensive manufacturing methods and often steep instrumentation requirements which must be considered unfit for industrial applications or measurement uses from a financial standpoint.

SUMMARY OF THE INVENTION

The problem of the present invention, against this background, is to improve a method and a device of the kind described in the introduction so that it is especially suitable for the spectroscopy of strongly absorbing media, has a high measurement sensitivity, and at the same time can be used on site, especially for online analysis, or at least can be produced at low cost.

The problem is solved according to the invention by a device for analyzing a fluid, comprising a waveguide, a source of electromagnetic radiation coupled to the waveguide on an entry side, and a detector coupled to the waveguide on an exit side for detecting electromagnetic radiation, wherein the waveguide is arranged in contact with the fluid in at least certain sections between its entry side and its exit side, wherein the device has an electrode arrangement, which is designed to generate an inhomogeneous electric field in a direct environment of the waveguide, suitable to exert a dielectrophoretic force on polarizable particles in the fluid, which moves these particles towards or away from the waveguide, wherein the electrode arrangement has a first electrode, which is arranged on the surface of the waveguide, and by a method for analyzing a fluid, comprising the steps of: coupling electromagnetic radiation to a waveguide on an entry side, arranged in contact with the fluid in at least certain sections, moves through it undergoing total internal reflection, and is coupled out and detected at an exit side, it being possible to detect an attenuation of the electromagnetic radiation, and generating an inhomogeneous electric field in the direct environment of the waveguide by an electrode arrangement, which has a first electrode arranged on the surface of the waveguide, which is suitable to exerting a dielectrophoretic force on polarizable particles in the fluid, which moves these particles towards or away from the waveguide. Advantageous modifications are the subject matter of the respective subclaims.

The method of the kind described at the outset is modified according to the invention in that a spatially inhomogeneous electric field is generated in the direct environment of the waveguide by means of an electrode arrangement, which has a first electrode arranged on the surface of the waveguide. which is suitable to exerting a dielectrophoretic force on polarizable particles in the fluid, which moves these particles towards or away from the waveguide. Accordingly, the device described at the outset furthermore has an electrode arrangement according to the invention, which is adapted to generating a spatially inhomogeneous electric field in the immediate environment of the waveguide, which field is suitable to exerting a dielectrophoretic force on polarizable particles in the fluid which moves these particles towards or away from the waveguide, while the electrode arrangement has a first electrode which is arranged on the surface of the waveguide.

In summary, the invention combines the method of evanescence field spectroscopy with dielectrophoresis such that, on the one hand, an enhanced sensitivity of the spectrometric method for detection of polarizable particles in the fluid under analysis is efficiently achieved, or on the other hand perturbing polarizable particles can be efficiently driven out from the evanescent field and thus the detection sensitivity for nonpolarizable particles is increased.

This occurs in an especially efficient and at the same time structurally simple manner because the first electrode arranged on the surface of the waveguide, which is or can be brought in contact with the fluid, has the effect that the electric field generated with the electrode arrangement has its largest field gradient as close as possible to this surface of the waveguide, so that the polarizable particles in the fluid are transported towards or away from it as efficiently as possible.

"On the surface" in the above sense does not necessarily mean in direct contact with the surface, but instead also includes configurations in which an intermediate layer or a spacing exists between the electrode and the waveguide, yet in any case it must be assured that the dielectrophoretic force concentrates the particles within the range of the evanescent field. Therefore, in most instances it is ultimately preferably for the first electrode to be placed on the surface of the waveguide in contact or able to be brought into contact with the fluid.

The method according to the invention and the device according to the invention are especially well suited, for example, to determining the water content in a fluid, such as a lubricant. The invention is based on the understanding that in the case of water contamination in lubricating oils the water is present in the form of tiny droplets above roughly 300 ppm. The fluid then forms an emulsion. These droplets are to be concentrated by means of the dielectrophoretic force in the range of influence of the evanescent field, thereby enhancing the measurement sensitivity of the device.

The study of emulsions itself opens up a broad field of application of lubrication engineering, such as the (online) assaying of lubricating oils in engines or transmissions, even in the cosmetics industry, such as the (online) monitoring of the ingredients of cosmetic products or intermediate products. The invention makes use of the advantages of evanescence field spectroscopy, namely, a practically isolated measurement of the radiation absorption without scatter losses and an extremely selective determination of selected absorption bands, which is particularly advantageous in fluids with large contents of contaminants or fillers.

But of course the invention is not confined to the study of emulsions. It can also detect solid ingredients in liquids (suspension) or solid or liquid ingredients in a gas (aerosol).

Therefore, the application possibilities are very diverse. As a further sample application one can mention the evanescent stimulation of fluorescence in cell analysis, which can in any case be refined by the method of the invention if the cells being analyzed can be concentrated by dielectrophoresis.

Preferably the waveguide is an optical fiber.

Optical fibers are industrially produced in a large bandwidth and are therefore available for various spectral ranges. Thus, for example, a sapphire fiber can be used advantageously for infrared light. Moreover, optical fibers have the advantage of being easily available and in most cases require no further treatment. In the case of a core/cladding fiber, in which only the core is considered the waveguide in the sense of the definition given above, it may be necessary however to free the fiber from the outer cladding, at least in the section where it comes in contact with the fluid, so that the fluid can contact the surface of the core.

According to one advantageous modification of the invention, the first electrode is structurized.

"Structurized" means here, in the most general functional sense, that the electrode arrangement is suitable for generating a spatially inhomogeneous field with largest field gradient at the first electrode and thus as close as possible to the surface of the waveguide in contact with the fluid or able to be brought into contact with it. In terms of spatial geometry, structurized means that alternating along the surface of the waveguide in at least one viewing direction at least one section of the first electrode follows at least one section of (uncovered) waveguide surface, which is or can be brought in contact with the fluid. In the most simple configuration, this can be implemented in the form of a wire placed thereon. The arrangement with several wires is also included, wherein the wire or wires can be arranged in a geometrical structure allowing for the geometrical peculiarities of the waveguide and/or its surrounding measurement region, for example, also in the form of a lattice or fabric. In the arrangement of the wire or wires, one also needs to consider achieving an adequate inhomogeneity of the electric field on the surface of the waveguide. The occupation of the waveguide by the first electrode should not be too dense, so that the surface remains sufficiently free for coupling to the evanescent field.

Especially preferably, the optical fiber can be combined with an electrode placed on the surface of the waveguide and making contact with it, so that the first electrode is configured in the form of a wire coiled around the optical fiber.

Once again, the benefit is the use of simple, standardized components. The wire is preferably coiled repeatedly in the manner of a helix around the optical fiber and only fixed at the ends of the wire, thus ensuring that no additional medium, such as an adhesive, prevents the operation of the method of the invention in the sensor region where the waveguide is in contact with the fluid.

The first electrode preferably has a thickness, in the case of a wire a diameter, of $\frac{1}{10}$ of the waveguide thickness, in the case of a fiber, $\frac{1}{10}$ of the fiber diameter, or less. In particular, the thickness or the diameter of the electrode is 100 µm or less and especially preferably 50 µm or less.

The thinner the wire, the closer the maximum inhomogeneity of the electric field comes to the surface of the waveguide and the more efficiently the dielectrophoretic force acts on the polarizable particles in the sensor region and accelerates them towards or away from the waveguide.

Alternatively to the applied first electrode, the first electrode can also be placed down in the form of a coating on the surface of the waveguide.

A coating has the advantage that one is more free in the design of the coating pattern than, say, in the case of an applied wire. What was said above holds for the geometrical design of the first coated electrode. However, it can be a drawback that a coating placed directly on the waveguide can for its part cause an attenuation of the electromagnetic radiation, whether by changing the index of refraction or by coupling to the evanescent field of a regularly reflected wave.

Therefore, a refraction-adapted layer is preferably arranged between the first coated electrode and the surface of the waveguide, which ensures a total reflection of the electromagnetic radiation in the waveguide.

One advantageous modification of the device calls for it to have a container for the fluid, wherein the waveguide is arranged in the container and can be brought into contact with the fluid. It is especially advantageous when the container is outfitted with one inlet and one outlet for the fluid, as a flow cell.

In this way, the method enables an assaying of a flowing fluid which passes through the waveguide during the analysis. The flow cell can also receive intermittent flow, for example, for filling it, and then be operated statically during the measurement and again receive a flow for the drainage. This variant solution is suitable both for mobile use on site and for permanent installation of the analysis layout, for example, in the oil circuit of an engine or the intake line for a fluid in a production facility.

If the container is designed as a flow cell and the waveguide as an optical fiber, the flow cell especially preferably has a tube concentrically surrounding the optical fiber.

This layout, again, is technically easy to implement and at the same time it is extremely efficient for online analysis.

The same holds for an electrode arrangement with a second electrode, which is fashioned as a hollow cylinder and in which the optical fiber is arranged concentrically.

A corresponding second electrode can in turn be arranged concentrically in the tube of the flow cell or constitute the latter.

The source for the electromagnetic radiation is especially preferably an infrared light source. Again, an electromagnetic radiation in the infrared with a half-width of 200 nm or less is preferably used.

On the one hand, an infrared light source emits radiation suitable for the determination of the water content in the fluid. A band with a half-width of 200 nm wavelength is narrow enough for the detection of absorption bands of water.

Moreover, the center wavelength of the electromagnetic radiation preferably lies in the range of 2.8 µm to 3.1 µm.

In consideration of the aforementioned half-width of 200 nm or less, the detection of water absorption bands at 2.95 µm wavelength is assured with the mentioned center wavelength.

In regard to cell analysis, a source for electromagnetic radiation in the visible and near UV range is preferably used, especially one which emits light with wavelengths of 200 nm to 780 nm. In this way, certain cells can be effectively stimulated to fluoresce. If the cells are polarizable, they are concentrated by the device of the invention in the evanescence field of the waveguide, where they absorb a portion of the energy and re-emit it as fluorescent radiation. Besides the absorption measurement, in this case a fluorescence measurement at the same time can furnish information about the analyzed specimen.

The required half-width is preferably achieved, regardless of the center wavelength, in that the source or the detector for the electromagnetic radiation is coordinated with an interference filter.

In this way, the desired wavelength and half-width can be adjusted, while a replacement of the filter enables a universal use of the device, given a sufficiently broad-band light source.

Preferably, the device has an alternating voltage source for supplying the electrode arrangement with an alternating voltage, so that an inhomogeneous alternating electric field is generated in the immediate environment of the waveguide.

The benefit of an alternating field as compared to a unidirectional field is that ionic substances in such a field are not accelerated in one direction or another, averaging over time. Thus, the concentration in an alternating electric field is solely due to the effect of dielectrophoresis and therefore pertains primarily to polarizable, uncharged particles.

BRIEF DESCRIPTION OF THE DRAWINGS

Further advantages and features of the invention are explained below by means of sample embodiments. The figures show FIG. 1, a first sample embodiment of the device according to the invention with an optical fiber waveguide;

FIG. 4, a spectrum of the signal attenuation as a function of the particle content with the inhomogeneous electric field switched off and switched on, and FIG. 5, a measurement of the absorbance of contaminated oil with different water contents, with and without dielectrophoresis switched on.

DETAILED DESCRIPTION OF THE INVENTION

Figure 1:
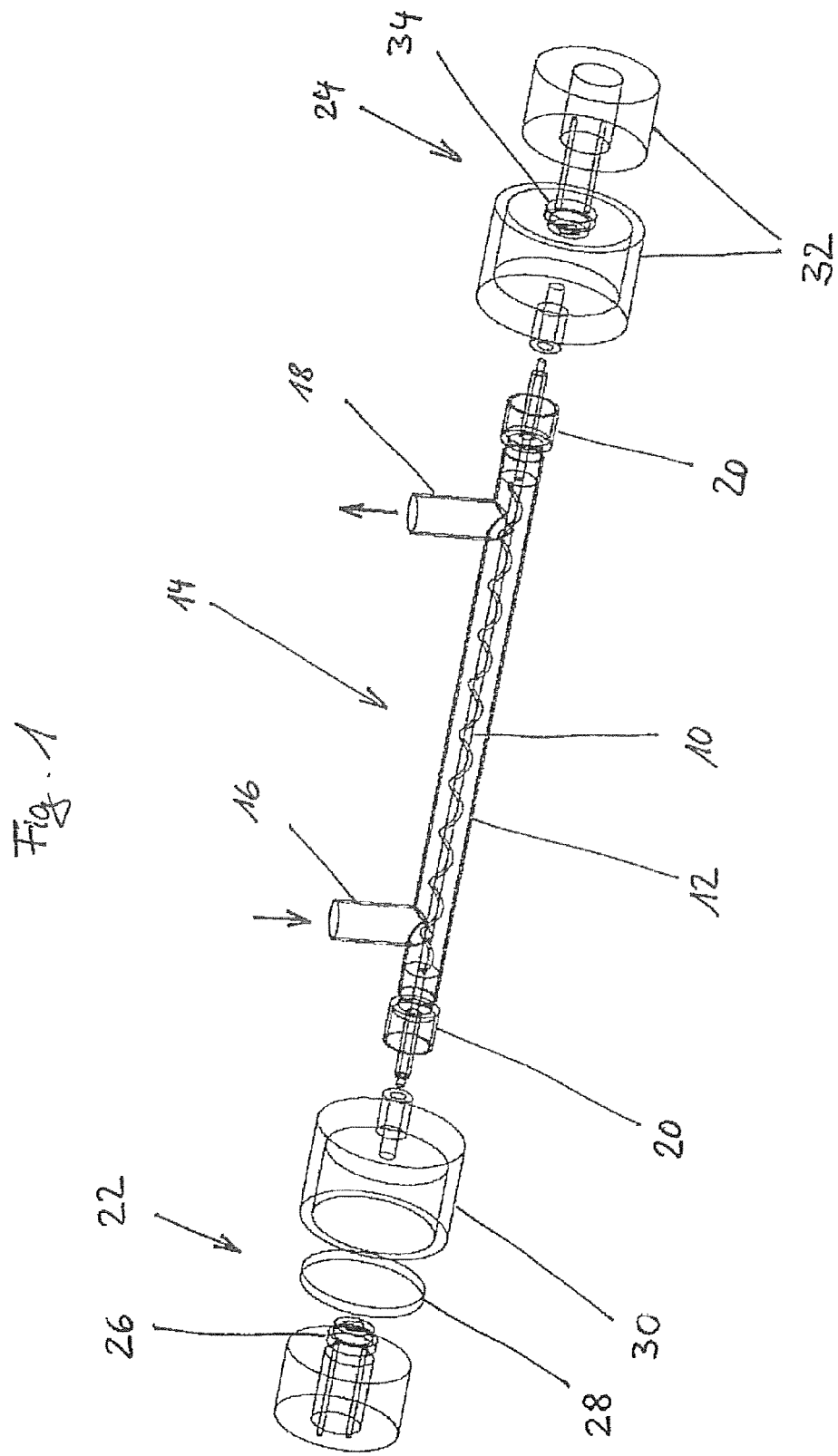

A sample embodiment of the device of the invention is shown in FIG. 1. The device has a waveguide in the form of an optical fiber 10, which is arranged concentrically in a tube 12 of a flow cell 14. The flow cell 14 moreover comprises an inlet 16 and an outlet 18 for the fluid being analyzed. The tube 12 of the flow cell 14 is sealed at both ends and has there a plug connection 20 for contacting an electrode arrangement 36.

Figure 2:
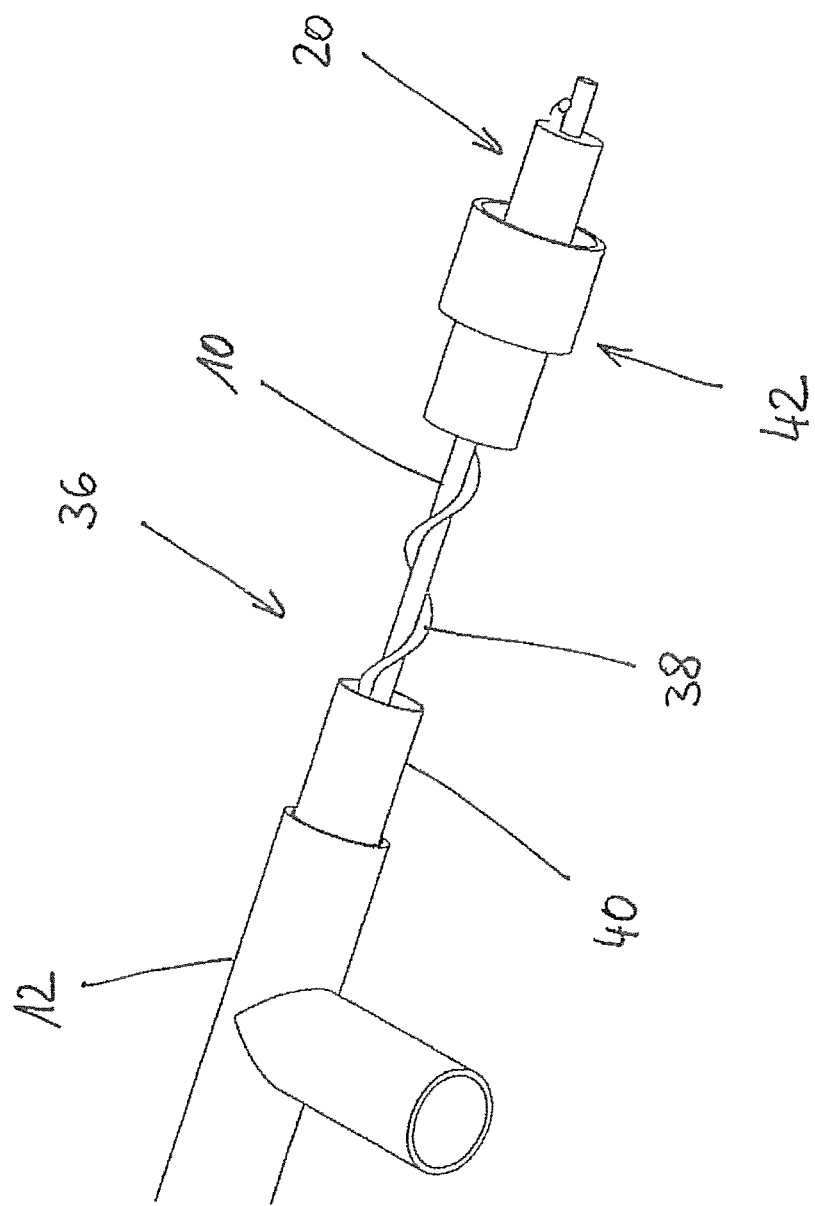
FIG. 2, a cutout from the device of FIG. 1 regarding the electrode arrangement.

Said electrode arrangement 36 is shown in detail in FIG. 2. It comprises a wirelike first electrode 38, which is wound in spiral or helical manner about the optical fiber 10. The first electrode 38, while continuous, nevertheless sections of the first electrode alternately follow uncovered sections of the waveguide surface looking in the direction of the longitudinal axis of the fiber 10 along the surface of the waveguide.

Figure 4:
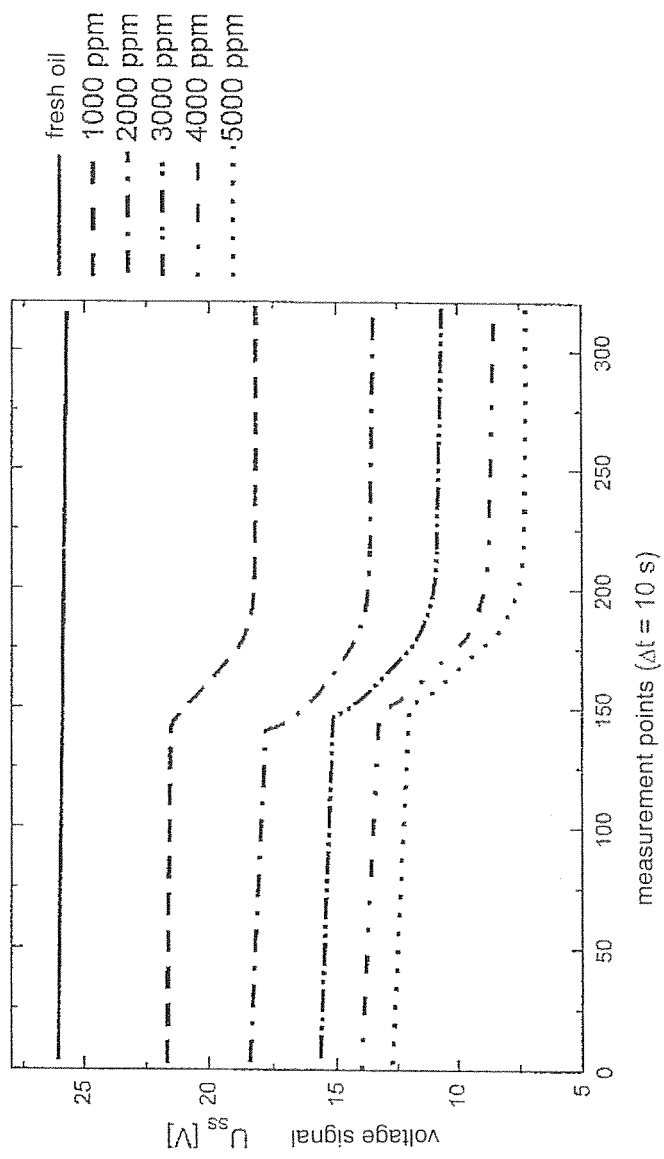

The electrode arrangement 36 furthermore comprises a tubular second electrode or counter electrode 40, which concentrically surrounds the optical fiber 10 inside the tube 12 of the flow cell 14. The wire 38 is only fixed, preferably glued, to the optical fiber 10 in a holder 42 at its start and at its end. The holders 42, moreover, fix the second tubular electrode 40. They are fashioned as a dielectric electrically insulating both ends of the electrode. The entire arrangement according to FIG. 4 is concentrically inserted into the tube 12 of the flow cell 14.

The optical fiber 10 is led through the two plug connections 20. At the entry end, it is coupled to a source 22 of electromagnetic radiation and at the exit end to a detector arrangement 24. The source 22 comprises an infrared (IR) radiation source 26. This radiation source 26 can be a thermal radiator, an LED, a laser diode or some other laser. The wavelength of the radiation source 26 depends on the spectral bands of the substance being analyzed and therefore need not emit predominantly in the infrared, as in this example. The source 22 moreover comprises a spectral filter 28, which is helpful especially in the case of broadband, such as thermal radiation sources, in cutting out the narrowest possible spectrum around the target wavelength and thereby enhancing the significance of the measurement. For narrow-band light sources, such as a laser, the filter can be eliminated. Finally, the source 22 comprises a housing 30, which accommodates the radiation source 26 and the filter 28.

The detector arrangement 24 likewise comprises a housing 32, in which a detector sensitive to the particular wavelength is arranged, here, an IR detector 34, and coupled to the exit end of the waveguide 10. The detector 34 is preferably a semiconductor detector, with which the absorption losses of the electromagnetic radiation in the evanescence field of the optical fiber 10 can be measured.

Figure 3:
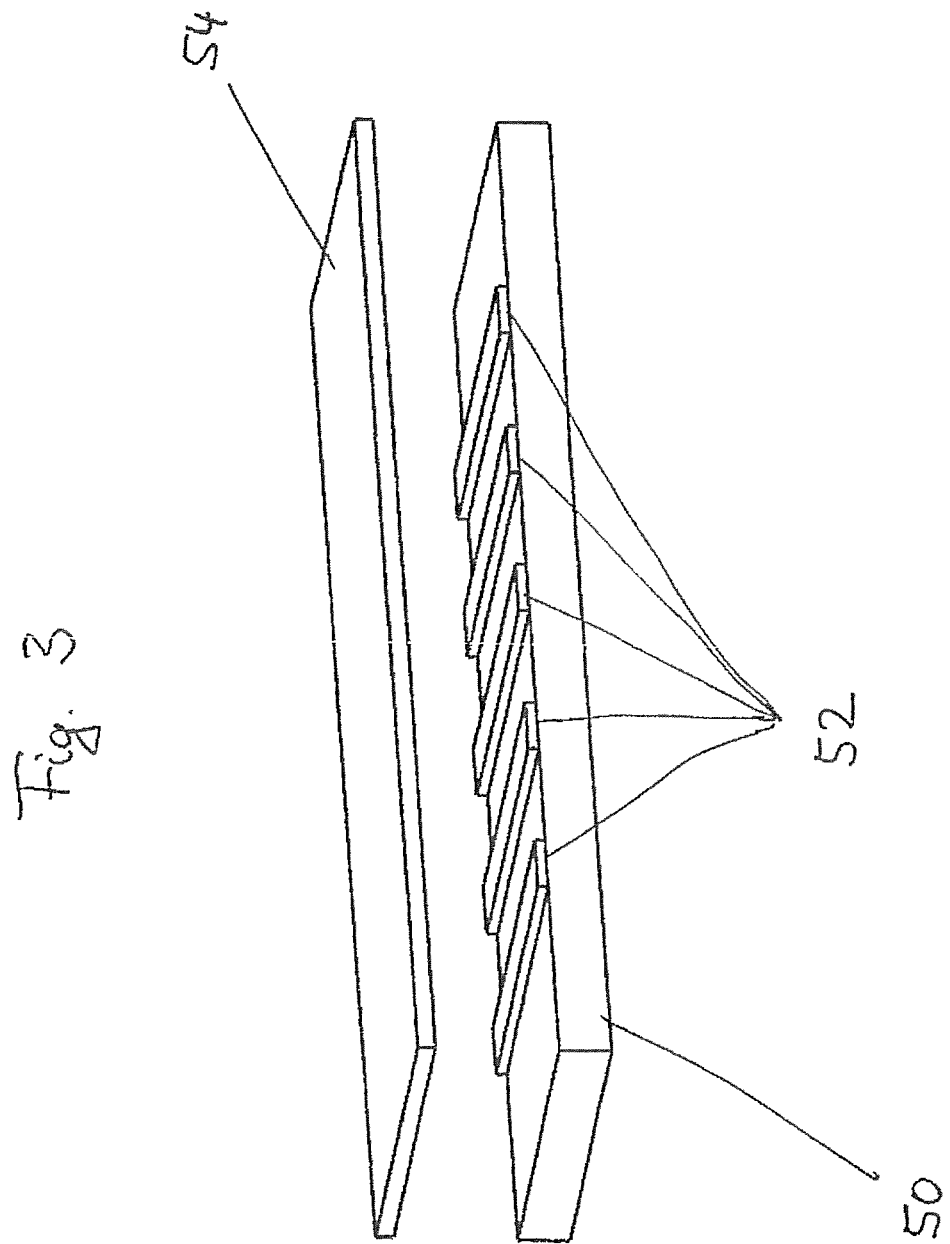
FIG. 3, a second sample embodiment of the device according to the invention with a planar waveguide.

In departure from the sample embodiment of FIGS. 1 and 2, a flat waveguide geometry for example can also be chosen, as is shown schematically and simplified in FIG. 3. The waveguide 50 here has the shape of a rectangular plate. On the plate are arranged several striplike, discontinuous sections of the first electrode 52 transversely to the lengthwise direction of the plate. At the side of the strips, with a parallel spacing, is arranged a second platelike electrode or counter electrode 54, having roughly the lateral dimensions of the waveguide 50. This configuration as well is designed to form an inhomogeneous electric field for the dielectrophoresis between the striplike electrodes 52 and the counter electrode 54 near the surface of the waveguide 50.

Such a flat geometry is especially interesting in regard to an integration of the analysis device of the invention in a lab-on-a-chip system. The waveguide 50, the electrodes 52, 54 and the container or the flow cell for the fluid being analyzed in the form of the intermediate space between the waveguide 50 and the counter electrode 54 can be formed here directly on the chip.

The geometrical circumstances of the two sample embodiments are examples and it is understood that the functionality of the invention can also be implemented with other waveguide and electrode arrangements, depending on the particular application.

In what follows, the method will be sketched out for the spectroscopic analysis of a liquid or gaseous analyte in the evanescence field of an optical fiber 10, as previously shown, or generally an ATR cell, which can also have a different waveguide geometry. Light of a wavelength corresponding to the absorption band being detected is coupled in at the entrance to the waveguide or fiber 10 and measured at the exit by a detector 34. If the analyte being investigated is situated in the active range of the evanescence field surrounding the waveguide 10—in the literature this is taken to be a region from the waveguide surface on the order of one wavelength of the light coupled in—one can determine the composition of the analyte by means of attenuation losses which are measured in the form of signal changes at the detector 34.

To improve the measurement sensitivity of the device, the concentration of the sought content substance in the analyte (such as water in oil) should be varied artificially at the measurement site, i.e., in the evanescence field of the wavelength 10, that is, it should be increased or decreased. This is done with the aid of dielectrophoresis, by which uncharged but polarizable particles are accelerated in the inhomogeneous electric field generated by the electrode arrangement 36. More precisely, the particles are oriented in the inhomogeneous electric field and experience a force in the direction of the higher field gradient in the case of positive dielectrophoresis. It should be noted that the dielectrophoresis can also be done using an alternating electromagnetic field. In this case, the sign of the force action depends on the frequency of the alternating field, according to the composition of the suspension, so that the polarizable contents and/or possibly the polarizable substrate of the fluid may be accelerated in opposite direction, i.e., in the direction of a decreasing field gradient.

Thus, for example, when the presence of water in oil (emulsion) causes an attenuation of the measurement signal, the effect can be enhanced by turning on the inhomogeneous electric field, because the water droplets thanks to the dielectrophoretic force move in the direction of the higher field gradient, i.e., the direction of the first electrode 38, and thus into the immediate vicinity of the waveguide 10.

FIG. 4 shows detector signals showing such an effect, plotted against time. Water in oil emulsions with different water concentrations were measured. For comparison, a measurement was done with uncontaminated oil ("fresh oil"). The curves from top to bottom show the absorption behavior of fresh oil and contaminated oils with 1000 ppm water, 2000 ppm water, 3000 ppm water, 4000 ppm water and 5000 ppm water.

At the left half of the measurement curves, the sensitivity of the analysis device without dielectrophoresis was determined. It is seen t hat the signal amplitude drops from around 26 V for the fresh oil to around 13 V for the oil with the highest water concentration. After around 150 seconds measurement duration, a potential difference was created between the electrodes. The offset in the five lower measurement curves now makes clear the influence of the dielectrophoresis. But since the upper fresh oil curve shows no change in trend after the inhomogeneous electric field is turned on, it can be concluded that the fresh oil contains no polarizable ingredients which could be influenced by the dielectrophoresis. In the five lower curves there is a significant drop-off in signal amplitude and thus a significantly higher absorption in the evanescence field, and this to an increasing degree with increasing water content.

The connection between the water content and the attenuation or absorbance with and without dielectrophoresis is again illustrated by FIG. 5. The plotted absorbance corresponds to the negative decimal logarithm of the intensity ratio of water-contaminated lubricating oil and water-free fresh oil. The water concentration is indicated in ppm. While the trend of the lower absorbance curve without the influence of dielectrophoresis is relatively flat under increasing water concentration in the oil, the slope of the upper absorbance curve becomes much more steep with the influence of dielectrophoresis. Since the steepness of the curves reflects the measurement sensitivity of the spectroscopic method, FIG. 4 thus proves a heightened measurement sensitivity of the method according to the invention and the device according to the invention.

At the same time, the device is also particularly suitable for online analysis for use on site and thanks to its simple design with easily obtainable standard components it can also be produced at low cost.

LIST OF REFERENCE SYMBOLS

10 Optical fiber/waveguide
12 Tube
14 Flow cell
16 Inlet
18 Outlet
20 Plug connection
22 Source
24 Detector arrangement
26 IR radiation source
28 Spectral filter
30 Housing
32 Housing
34 Detector
36 Electrode arrangement
38 Wirelike first electrode
40 Tubular second electrode/counter electrode
42 Holder
50 Waveguide
52 Striplike first electrode
54 Second electrode/counter electrode

What is claimed is:

1. A device for analyzing a fluid, comprising: an optical fiber, a source of electromagnetic radiation coupled to the optical fiber on an entry side, and a detector coupled to the optical fiber on an exit side for detecting electromagnetic radiation, wherein the optical fiber is arranged in contact with the fluid in at least certain sections between its entry side and its exit side, wherein the device has an electrode arrangement, which is designed to generate an inhomogeneous electric field in a direct environment of the optical fiber, suitable to exert a dielectrophoretic force on polarizable particles in the fluid, which moves these particles towards or away from the optical fiber, wherein the electrode arrangement has a first electrode, which is arranged on the surface of the optical fiber.

2. The device according to claim 1, wherein the first electrode is structurized.

3. The device according to claim 2, wherein the first electrode is applied in the form of a coating to the surface of the optical fiber.

4. The device according to claim 3, wherein a refraction-adapted layer is arranged between the coating of the first electrode and the surface of the optical fiber, which ensures a total reflection of the electromagnetic radiation in the optical fiber.

5. The device according to claim 1, wherein the first electrode lies in contact with the surface of the optical fiber.

6. The device according to claim 1, wherein the first electrode lies in contact with the surface of the optical fiber, and wherein the first electrode is in the form of a wire coiled around the optical fiber.

7. The device according to claim 1, further including a container for the fluid, wherein the optical fiber is arranged in the container and can be brought into contact with the fluid.

8. The device according to claim 7, wherein the container is configured as a flow cell with one inlet and one outlet for the fluid.

9. The device according to claim 8, wherein the flow cell has a tube concentrically surrounding the optical fiber.

10. The device according to claim 1, wherein the electrode arrangement has a second electrode, which is configured as a hollow cylinder and in which the optical fiber is arranged concentrically.

11. The device according to claim 1, further including an alternating voltage source for supplying the electrode arrangement with an alternating voltage.

12. The device according to claim 1, wherein the first electrode is structurized, and wherein the first electrode lies in contact with the surface of the optical fiber.

13. The device according to claim 12, wherein the first electrode is in the form of a wire coiled around the optical fiber.

14. The device according to claim 13, further including a container for the fluid, wherein the optical fiber is arranged in the container and can be brought into contact with the fluid, and wherein the container is configured as a flow cell with one inlet and one outlet for the fluid.

15. The device according to claim 14, further including an alternating voltage source for supplying the electrode arrangement with an alternating voltage.

16. A method for analyzing a fluid, comprising the steps of:
coupling electromagnetic radiation to an optical fiber on an entry side, arranged in contact with the fluid in at least certain sections, moves through it undergoing total internal reflection, and is coupled out and detected at an exit side, it being possible to detect an attenuation of the electromagnetic radiation, and generating an inhomogeneous electric field in the direct environment of the optical fiber by an electrode arrangement, which has a first electrode arranged on the surface of the optical fiber which is suitable to exerting a dielectrophoretic force on polarizable particles in the fluid, which moves these particles towards or away from the optical fiber.

17. The method according to claim 16, wherein an inhomogeneous alternating electric field is generated.

18. The method according to claim 17, wherein the fluid passes through the optical fiber during the analysis.

19. The method according claim 16, wherein the fluid passes through the optical fiber during the analysis.

* * * * *